United States Patent
Melanson et al.

(10) Patent No.: US 8,801,647 B2
(45) Date of Patent: Aug. 12, 2014

(54) USE OF A GASTROINTESTINAL SLEEVE TO TREAT BARIATRIC SURGERY FISTULAS AND LEAKS

(75) Inventors: David A. Melanson, Hudson, NH (US); Manoel dos Passos Galvao Neto, Guarlhos (BR)

(73) Assignee: GI Dynamics, Inc., Lexington, MA (US)

( * ) Notice: Subject to any disclaimer, the term of this patent is extended or adjusted under 35 U.S.C. 154(b) by 398 days.

(21) Appl. No.: 12/070,912

(22) Filed: Feb. 21, 2008

(65) Prior Publication Data
US 2008/0208357 A1   Aug. 28, 2008

Related U.S. Application Data

(60) Provisional application No. 60/902,705, filed on Feb. 22, 2007, provisional application No. 61/005,437, filed on Dec. 5, 2007.

(51) Int. Cl.
*A61F 2/04* (2013.01)
*A61F 5/00* (2006.01)

(52) U.S. Cl.
CPC ............... *A61F 5/0076* (2013.01); *A61F 2/04* (2013.01); *A61F 2002/044* (2013.01); *A61F 5/0013* (2013.01); *A61F 5/0079* (2013.01); *A61F 5/0083* (2013.01)
USPC ................. 604/8; 604/9; 604/10; 623/1.11; 623/1.12; 623/23.64

(58) Field of Classification Search
CPC ... A61F 2/04; A61F 2002/044; A61F 5/0013; A61F 5/0076; A61F 5/0079; A61F 5/0083; A61F 5/0086; A61F 5/0036; A61F 2005/0003; A61F 2005/0013; A61B 17/1114
USPC ............ 604/8; 623/23.64, 23.65, 23.7, 23.75, 623/23.76; 606/108
See application file for complete search history.

(56) References Cited

U.S. PATENT DOCUMENTS

| 1,899,781 A | 2/1933 | Twiss |
| 2,464,933 A | 3/1949 | Kaslow |

(Continued)

FOREIGN PATENT DOCUMENTS

| DE | 33 26 061 A1 | 2/1984 |
| EP | 0 480 667 B1 | 4/1992 |

(Continued)

OTHER PUBLICATIONS

Gray, Henry, "The Vascular System," In Anatomy, Descriptive and Surgical, 15th Edition, (Bounty Books:NY), T.P. Pick and R. Howden, eds., pp. 1126-1128 (1977).

(Continued)

*Primary Examiner* — Adam Marcetich
(74) *Attorney, Agent, or Firm* — Hamilton Brook Smith & Reynolds, PC

(57) ABSTRACT

Method for treating a Roux-en-Y patient having fistulas and leaks as a result of bariatric surgery. A gastrointestinal implant device is anchored in the esophagus and extends through a stomach pouch into an intestine anastomosed to the stomach pouch to prevent fistulas and other damaged tissue from making contact with food and fluids entering the esophagus. The gastrointestinal implant device includes an unsupported flexible sleeve and an anchor coupled to a proximal portion of the sleeve. The flexible sleeve is open at both ends, and adapted to extend below a jejunum. The anchor is adapted to be retained within the esophagus, preferably just above the gastroesophageal (GE) Junction. The anchor can include a stent such as a wave anchor and is collapsible for catheter-based delivery and removal.

12 Claims, 11 Drawing Sheets

(56) References Cited

U.S. PATENT DOCUMENTS

| | | |
|---|---|---|
| 3,780,740 A | 12/1973 | Rhea |
| 4,133,315 A | 1/1979 | Berman et al. |
| 4,134,405 A | 1/1979 | Smit |
| 4,246,893 A | 1/1981 | Berson |
| 4,265,694 A | 5/1981 | Boretos et al. |
| 4,270,542 A | 6/1981 | Plumley |
| 4,271,827 A | 6/1981 | Angelchik |
| 4,279,251 A | 7/1981 | Rüsch |
| 4,315,509 A | 2/1982 | Smit |
| 4,341,218 A | 7/1982 | Hoi |
| 4,403,604 A | 9/1983 | Wilkinson et al. |
| 4,416,267 A | 11/1983 | Garren et al. |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,763,653 A | 8/1988 | Rockey |
| 4,768,507 A | 9/1988 | Fischell et al. |
| 4,823,808 A | 4/1989 | Clegg et al. |
| 4,846,836 A | 7/1989 | Reich |
| 4,878,905 A | 11/1989 | Blass |
| 4,905,693 A * | 3/1990 | Ravo .................. 606/153 |
| 4,913,141 A | 4/1990 | Hillstead |
| 5,035,706 A | 7/1991 | Gianturco et al. |
| 5,037,387 A | 8/1991 | Quinn et al. |
| 5,041,126 A | 8/1991 | Gianturco |
| 5,057,091 A | 10/1991 | Andersen |
| 5,059,166 A | 10/1991 | Fischell et al. |
| 5,104,399 A | 4/1992 | Lazarus |
| 5,123,917 A | 6/1992 | Lee |
| 5,135,516 A | 8/1992 | Sahatjian et al. |
| 5,152,756 A | 10/1992 | Quinn et al. |
| 5,152,782 A | 10/1992 | Kowligi et al. |
| 5,176,617 A | 1/1993 | Fischell et al. |
| 5,190,561 A | 3/1993 | Graber |
| 5,236,423 A | 8/1993 | Mix et al. |
| 5,246,456 A | 9/1993 | Wilkinson |
| 5,254,133 A | 10/1993 | Seid |
| 5,279,553 A | 1/1994 | Winkler et al. |
| 5,282,824 A | 2/1994 | Gianturco |
| 5,290,294 A | 3/1994 | Cox et al. |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,322,501 A | 6/1994 | Mahmud-Durrani |
| 5,330,500 A | 7/1994 | Song |
| 5,364,353 A | 11/1994 | Corfitsen et al. |
| 5,387,235 A | 2/1995 | Chuter |
| 5,389,090 A | 2/1995 | Fischell et al. |
| 5,401,241 A | 3/1995 | Delany |
| 5,405,378 A | 4/1995 | Strecker |
| 5,417,697 A | 5/1995 | Wilk et al. |
| 5,443,498 A | 8/1995 | Fontaine |
| 5,456,713 A | 10/1995 | Chuter |
| 5,480,423 A | 1/1996 | Ravenscroft et al. |
| 5,492,530 A | 2/1996 | Fischell et al. |
| 5,507,767 A | 4/1996 | Maeda et al. |
| 5,507,771 A | 4/1996 | Gianturco |
| 5,522,880 A | 6/1996 | Barone et al. |
| 5,562,697 A | 10/1996 | Christiansen |
| 5,569,219 A | 10/1996 | Hakki et al. |
| 5,571,173 A | 11/1996 | Parodi |
| 5,605,530 A | 2/1997 | Fischell et al. |
| 5,607,442 A | 3/1997 | Fischell et al. |
| 5,611,787 A | 3/1997 | Demeter et al. |
| 5,624,430 A | 4/1997 | Eton et al. |
| 5,630,797 A | 5/1997 | Diedrich et al. |
| 5,634,928 A | 6/1997 | Fischell et al. |
| 5,639,274 A | 6/1997 | Fischell et al. |
| 5,643,312 A | 7/1997 | Fischell et al. |
| 5,662,713 A | 9/1997 | Andersen et al. |
| 5,665,064 A | 9/1997 | Bodicky et al. |
| 5,669,932 A | 9/1997 | Fischell et al. |
| 5,690,642 A | 11/1997 | Osborne et al. |
| 5,693,084 A | 12/1997 | Chuter |
| 5,695,516 A | 12/1997 | Fischell et al. |
| 5,697,971 A | 12/1997 | Fischell et al. |
| 5,713,948 A | 2/1998 | Uflacker |
| 5,715,832 A | 2/1998 | Koblish et al. |
| 5,720,776 A | 2/1998 | Chuter et al. |
| 5,722,984 A | 3/1998 | Fischell et al. |
| 5,730,698 A | 3/1998 | Fischell et al. |
| 5,733,325 A | 3/1998 | Robinson et al. |
| 5,735,859 A | 4/1998 | Fischell et al. |
| 5,735,892 A | 4/1998 | Myers et al. |
| 5,743,874 A | 4/1998 | Fischell et al. |
| 5,749,825 A | 5/1998 | Fischell et al. |
| 5,755,777 A | 5/1998 | Chuter |
| 5,759,174 A | 6/1998 | Fischell et al. |
| 5,776,186 A | 7/1998 | Uflacker |
| 5,792,144 A | 8/1998 | Fischell et al. |
| 5,792,172 A | 8/1998 | Fischell et al. |
| 5,800,456 A | 9/1998 | Maeda et al. |
| 5,800,526 A | 9/1998 | Anderson et al. |
| 5,820,584 A | 10/1998 | Crabb |
| 5,830,229 A | 11/1998 | Konya et al. |
| 5,840,009 A | 11/1998 | Fischell et al. |
| 5,843,164 A | 12/1998 | Frantzen et al. |
| 5,855,601 A | 1/1999 | Bessler et al. |
| 5,861,036 A * | 1/1999 | Godin .................. 623/23.64 |
| 5,876,445 A | 3/1999 | Andersen et al. |
| 5,879,282 A | 3/1999 | Fischell et al. |
| 5,879,370 A | 3/1999 | Fischell et al. |
| 5,895,391 A | 4/1999 | Farnholtz |
| 5,910,145 A | 6/1999 | Fischell et al. |
| 5,913,895 A | 6/1999 | Burpee et al. |
| 5,919,233 A | 7/1999 | Knopf et al. |
| 5,925,063 A | 7/1999 | Khosravi |
| 5,962,620 A | 10/1999 | Reich et al. |
| 5,963,620 A | 10/1999 | Frankel et al. |
| 5,964,771 A | 10/1999 | Beyar et al. |
| 5,976,153 A | 11/1999 | Fischell et al. |
| 6,013,019 A | 1/2000 | Fischell et al. |
| 6,027,508 A | 2/2000 | Ren et al. |
| 6,027,526 A | 2/2000 | Limon et al. |
| 6,035,856 A | 3/2000 | LaFontaine et al. |
| 6,074,673 A | 6/2000 | Guillen |
| 6,086,604 A | 7/2000 | Fischell et al. |
| 6,099,552 A | 8/2000 | Adams |
| 6,102,887 A | 8/2000 | Altman |
| 6,120,533 A | 9/2000 | Fischell |
| 6,120,534 A | 9/2000 | Ruiz |
| 6,132,471 A | 10/2000 | Johlin, Jr. |
| 6,146,323 A | 11/2000 | Fischell |
| 6,152,956 A | 11/2000 | Pierce |
| 6,179,868 B1 | 1/2001 | Burpee et al. |
| 6,187,016 B1 | 2/2001 | Hedges et al. |
| 6,190,403 B1 | 2/2001 | Fischell et al. |
| 6,200,336 B1 | 3/2001 | Pavcnik et al. |
| 6,221,043 B1 | 4/2001 | Fischell et al. |
| 6,221,102 B1 | 4/2001 | Baker et al. |
| 6,241,738 B1 | 6/2001 | Dereume |
| 6,241,757 B1 | 6/2001 | An et al. |
| 6,251,064 B1 | 6/2001 | Silverman et al. |
| 6,251,132 B1 | 6/2001 | Ravenscroft et al. |
| 6,264,700 B1 * | 7/2001 | Kilcoyne et al. .......... 623/23.68 |
| 6,270,521 B1 | 8/2001 | Fischell et al. |
| 6,293,960 B1 | 9/2001 | Ken |
| 6,302,891 B1 | 10/2001 | Nadal |
| 6,302,917 B1 | 10/2001 | Dua et al. |
| 6,315,708 B1 | 11/2001 | Salmon et al. |
| 6,322,538 B1 | 11/2001 | Elbert et al. |
| 6,331,190 B1 | 12/2001 | Shokoohi et al. |
| 6,332,877 B1 | 12/2001 | Michels |
| 6,355,056 B1 | 3/2002 | Pinheiro |
| 6,356,782 B1 | 3/2002 | Sirimanne et al. |
| 6,375,660 B1 | 4/2002 | Fischell et al. |
| 6,383,214 B1 | 5/2002 | Banas et al. |
| 6,387,114 B2 | 5/2002 | Adams |
| 6,401,718 B1 | 6/2002 | Johnson et al. |

(56) References Cited

U.S. PATENT DOCUMENTS

| | | |
|---|---|---|
| 6,402,779 B1 | 6/2002 | Colone et al. |
| 6,406,792 B1 | 6/2002 | Briquet et al. |
| 6,428,558 B1 | 8/2002 | Jones et al. |
| 6,450,989 B2 | 9/2002 | Dubrul et al. |
| 6,458,074 B1 | 10/2002 | Matsui et al. |
| 6,485,409 B1 | 11/2002 | Voloshin et al. |
| 6,485,515 B2 | 11/2002 | Strecker |
| 6,508,833 B2 | 1/2003 | Pavcnik et al. |
| 6,520,985 B1 | 2/2003 | Burpee et al. |
| 6,524,335 B1 | 2/2003 | Hartley et al. |
| 6,524,336 B1 | 2/2003 | Papazolgou et al. |
| 6,530,951 B1 | 3/2003 | Bates et al. |
| 6,537,247 B2 | 3/2003 | Shannon |
| 6,540,775 B1 | 4/2003 | Fischell et al. |
| 6,540,789 B1 | 4/2003 | Silverman et al. |
| 6,544,291 B2 | 4/2003 | Taylor |
| 6,547,817 B1 | 4/2003 | Fischell et al. |
| 6,558,400 B2 | 5/2003 | Deem et al. |
| 6,558,429 B2 | 5/2003 | Taylor |
| 6,565,597 B1 | 5/2003 | Fearnot et al. |
| 6,589,213 B2 | 7/2003 | Reydel |
| 6,589,275 B1 | 7/2003 | Ivancev et al. |
| 6,623,518 B2 | 9/2003 | Thompson et al. |
| 6,635,069 B1 | 10/2003 | Teoh et al. |
| 6,635,079 B2 | 10/2003 | Unsworth et al. |
| 6,645,239 B1 | 11/2003 | Park et al. |
| 6,652,555 B1 | 11/2003 | VanTassel et al. |
| 6,656,194 B1 | 12/2003 | Gannoe et al. |
| 6,669,722 B2 | 12/2003 | Chen et al. |
| 6,675,809 B2 | 1/2004 | Stack et al. |
| 6,676,692 B2 | 1/2004 | Rabkin et al. |
| 6,695,875 B2 | 2/2004 | Stelter et al. |
| 6,699,263 B2 | 3/2004 | Cope |
| 6,699,278 B2 | 3/2004 | Fischell et al. |
| 6,706,061 B1 | 3/2004 | Fischell et al. |
| 6,716,240 B2 | 4/2004 | Fischell et al. |
| 6,736,840 B2 | 5/2004 | Fischell et al. |
| 6,740,121 B2 | 5/2004 | Geitz |
| 6,755,869 B2 | 6/2004 | Geitz |
| 6,764,518 B2 | 7/2004 | Godin |
| 6,773,440 B2 | 8/2004 | Gannoe et al. |
| 6,776,791 B1 | 8/2004 | Stallings et al. |
| 6,802,868 B2 | 10/2004 | Silverman et al. |
| 6,821,291 B2 | 11/2004 | Bolea et al. |
| 6,845,776 B2 | 1/2005 | Stack et al. |
| 6,860,901 B1 | 3/2005 | Baker et al. |
| 6,936,065 B2 | 8/2005 | Khan et al. |
| 6,960,233 B1 | 11/2005 | Berg et al. |
| 7,011,673 B2 | 3/2006 | Fischell et al. |
| 7,025,791 B2 | 4/2006 | Levine et al. |
| 7,033,384 B2 | 4/2006 | Gannoe et al. |
| 7,037,327 B2 | 5/2006 | Salmon et al. |
| 7,037,344 B2 | 5/2006 | Kagan et al. |
| 7,081,132 B2 | 7/2006 | Cook et al. |
| 7,087,088 B2 | 8/2006 | Berg et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,211,114 B2 | 5/2007 | Bessler et al. |
| 7,220,237 B2* | 5/2007 | Gannoe et al. ................ 604/8 |
| 7,220,284 B2 | 5/2007 | Kagan et al. |
| 7,267,694 B2 | 9/2007 | Levine et al. |
| 7,314,489 B2 | 1/2008 | McKenna et al. |
| 7,329,285 B2 | 2/2008 | Levine et al. |
| 7,338,520 B2 | 3/2008 | Bailey et al. |
| 7,347,875 B2 | 3/2008 | Levine et al. |
| 7,354,454 B2 | 4/2008 | Stack et al. |
| 7,476,256 B2 | 1/2009 | Meade et al. |
| 2001/0020190 A1 | 9/2001 | Taylor |
| 2002/0022853 A1 | 2/2002 | Swanson et al. |
| 2002/0032487 A1 | 3/2002 | Dua et al. |
| 2002/0065545 A1 | 5/2002 | Leonhardt et al. |
| 2002/0091439 A1 | 7/2002 | Baker et al. |
| 2002/0120277 A1 | 8/2002 | Hauschild et al. |
| 2002/0143387 A1 | 10/2002 | Soetikno et al. |
| 2002/0147489 A1 | 10/2002 | Hong et al. |
| 2002/0151953 A1 | 10/2002 | Chobotov et al. |
| 2002/0177890 A1 | 11/2002 | Lenker |
| 2002/0183768 A1 | 12/2002 | Deem et al. |
| 2002/0183786 A1 | 12/2002 | Girton |
| 2002/0188344 A1 | 12/2002 | Bolea et al. |
| 2002/0193828 A1 | 12/2002 | Griffin et al. |
| 2003/0032941 A1 | 2/2003 | Boyle et al. |
| 2003/0040804 A1 | 2/2003 | Stack et al. |
| 2003/0040808 A1 | 2/2003 | Stack et al. |
| 2003/0050684 A1 | 3/2003 | Abrams et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0149467 A1 | 8/2003 | Linder et al. |
| 2003/0153927 A1 | 8/2003 | DiPoto et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0216749 A1 | 11/2003 | Ishikawa et al. |
| 2003/0233140 A1 | 12/2003 | Hartley et al. |
| 2004/0019388 A1 | 1/2004 | Starkebaum |
| 2004/0024386 A1 | 2/2004 | Deem et al. |
| 2004/0037865 A1 | 2/2004 | Miller |
| 2004/0039452 A1 | 2/2004 | Bessler |
| 2004/0044357 A1 | 3/2004 | Gannoe et al. |
| 2004/0082963 A1* | 4/2004 | Gannoe et al. ................ 606/153 |
| 2004/0092892 A1 | 5/2004 | Kagan et al. |
| 2004/0092974 A1* | 5/2004 | Gannoe et al. ................ 606/153 |
| 2004/0093065 A1 | 5/2004 | Yachia et al. |
| 2004/0098079 A1 | 5/2004 | Hartley et al. |
| 2004/0107004 A1 | 6/2004 | Levine et al. |
| 2004/0117004 A1 | 6/2004 | Osborne et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122470 A1 | 6/2004 | Deem et al. |
| 2004/0133147 A1* | 7/2004 | Woo ................................ 604/9 |
| 2004/0136971 A1 | 7/2004 | Scharp et al. |
| 2004/0138525 A1 | 7/2004 | Saadat et al. |
| 2004/0138529 A1 | 7/2004 | Wiltshire et al. |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158229 A1 | 8/2004 | Quinn |
| 2004/0158331 A1 | 8/2004 | Stack et al. |
| 2004/0172063 A1 | 9/2004 | Li et al. |
| 2004/0172088 A1 | 9/2004 | Knudson et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0181242 A1 | 9/2004 | Stack et al. |
| 2004/0193093 A1 | 9/2004 | Desmond, III |
| 2004/0210243 A1 | 10/2004 | Gannoe et al. |
| 2004/0220682 A1 | 11/2004 | Levine et al. |
| 2004/0236401 A1 | 11/2004 | Shin et al. |
| 2004/0249362 A1 | 12/2004 | Levine et al. |
| 2005/0004681 A1 | 1/2005 | Stack et al. |
| 2005/0043601 A1 | 2/2005 | Kilcoyne et al. |
| 2005/0043817 A1 | 2/2005 | McKenna et al. |
| 2005/0049718 A1* | 3/2005 | Dann et al. ................ 623/23.65 |
| 2005/0055039 A1 | 3/2005 | Burnett et al. |
| 2005/0060017 A1 | 3/2005 | Fischell et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0085787 A1 | 4/2005 | Laufer |
| 2005/0085923 A1 | 4/2005 | Levine et al. |
| 2005/0090873 A1 | 4/2005 | Imran |
| 2005/0096673 A1* | 5/2005 | Stack et al. ................ 606/151 |
| 2005/0096750 A1 | 5/2005 | Kagan et al. |

(56) References Cited

U.S. PATENT DOCUMENTS

| | | | |
|---|---|---|---|
| 2005/0125020 A1* | 6/2005 | Meade et al. | 606/191 |
| 2005/0125075 A1 | 6/2005 | Meade et al. | |
| 2005/0149114 A1 | 7/2005 | Cartledge et al. | |
| 2005/0171556 A1 | 8/2005 | Murphy | |
| 2005/0192614 A1 | 9/2005 | Binmoeller | |
| 2005/0216040 A1 | 9/2005 | Gertner et al. | |
| 2005/0216042 A1 | 9/2005 | Gertner | |
| 2005/0221072 A1 | 10/2005 | Dubrow et al. | |
| 2005/0228415 A1 | 10/2005 | Gertner | |
| 2005/0228504 A1 | 10/2005 | Demarais | |
| 2005/0240279 A1 | 10/2005 | Kagan et al. | |
| 2005/0256587 A1 | 11/2005 | Egan | |
| 2005/0267499 A1 | 12/2005 | Stack et al. | |
| 2005/0267533 A1 | 12/2005 | Gertner | |
| 2006/0009858 A1 | 1/2006 | Levine et al. | |
| 2006/0064120 A1 | 3/2006 | Levine et al. | |
| 2006/0106332 A1 | 5/2006 | Knudson et al. | |
| 2006/0155312 A1 | 7/2006 | Levine et al. | |
| 2006/0157067 A1* | 7/2006 | Saadat et al. | 128/898 |
| 2006/0161139 A1* | 7/2006 | Levine et al. | 606/1 |
| 2006/0161172 A1 | 7/2006 | Levine et al. | |
| 2006/0161187 A1 | 7/2006 | Levine et al. | |
| 2006/0161265 A1 | 7/2006 | Levine et al. | |
| 2006/0212042 A1 | 9/2006 | Lamport et al. | |
| 2006/0265082 A1 | 11/2006 | Meade et al. | |
| 2006/0287734 A1 | 12/2006 | Stack et al. | |
| 2006/0293742 A1* | 12/2006 | Dann et al. | 623/1.11 |
| 2007/0005147 A1 | 1/2007 | Levine et al. | |
| 2007/0010864 A1 | 1/2007 | Dann et al. | |
| 2007/0027548 A1 | 2/2007 | Levine et al. | |
| 2007/0032879 A1 | 2/2007 | Levine et al. | |
| 2007/0049801 A1 | 3/2007 | Lamport et al. | |
| 2007/0083271 A1 | 4/2007 | Levine et al. | |
| 2007/0088389 A1* | 4/2007 | Dunkin et al. | 606/219 |
| 2007/0293716 A1* | 12/2007 | Baker et al. | 600/37 |
| 2008/0071383 A1 | 3/2008 | Levine | |
| 2008/0097466 A1 | 4/2008 | Levine et al. | |
| 2008/0103604 A1 | 5/2008 | Levine et al. | |
| 2008/0161787 A1* | 7/2008 | Roslin | 606/32 |
| 2008/0223476 A1 | 9/2008 | Stinson | |
| 2008/0234834 A1 | 9/2008 | Meade et al. | |
| 2008/0269715 A1* | 10/2008 | Faller et al. | 604/506 |
| 2009/0012544 A1 | 1/2009 | Thompson et al. | |

FOREIGN PATENT DOCUMENTS

| | | |
|---|---|---|
| EP | 0278937 B1 | 10/1993 |
| EP | 0 506 918 B1 | 1/1996 |
| EP | 0754017 B1 | 1/1997 |
| EP | 0843538 B1 | 5/1998 |
| EP | 0 857 471 A2 | 8/1998 |
| EP | 0935977 A2 | 8/1999 |
| EP | 0935977 A3 | 8/1999 |
| EP | 1 481 649 A1 | 12/2004 |
| EP | 1 504 778 A2 | 2/2005 |
| EP | 1 504 778 A3 | 3/2005 |
| JP | 04212348 | 8/1992 |
| WO | WO 92/06734 A1 | 4/1992 |
| WO | WO 97/03624 A1 | 2/1997 |
| WO | WO 00/12027 | 3/2000 |
| WO | WO 00/28922 A1 | 5/2000 |
| WO | WO 00/32137 | 6/2000 |
| WO | WO 00/42945 A1 | 7/2000 |
| WO | WO 00/42949 | 7/2000 |
| WO | WO 01/12256 A1 | 2/2001 |
| WO | WO 01/35861 A1 | 5/2001 |
| WO | WO 01/45485 A2 | 6/2001 |
| WO | WO 02/081019 A1 | 10/2002 |
| WO | WO 02/096327 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 03/086360 A1 | 10/2003 |
| WO | WO 03/094785 A1 | 11/2003 |
| WO | WO 2004/000169 A1 | 12/2003 |
| WO | WO 2004/004542 A2 | 1/2004 |
| WO | WO 2004/004542 A3 | 1/2004 |
| WO | WO 2004/014237 A3 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064680 A1 | 8/2004 |
| WO | WO 2004/064682 A1 | 8/2004 |
| WO | WO 2004/064685 A1 | 8/2004 |
| WO | WO 2004/069331 A2 | 8/2004 |
| WO | WO 2004/069332 A1 | 8/2004 |
| WO | WO 2004/073782 A1 | 9/2004 |
| WO | WO 2004/087014 A2 | 10/2004 |
| WO | WO 2004/087233 A2 | 10/2004 |
| WO | WO 2004/093639 A2 | 11/2004 |
| WO | WO 2004/093639 A3 | 11/2004 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/117716 A2 | 12/2005 |
| WO | WO 2005/118049 A1 | 12/2005 |
| WO | WO 2005/120363 A1 | 12/2005 |
| WO | WO 2006/016894 A1 | 2/2006 |
| WO | WO 2006/034062 A1 | 3/2006 |
| WO | WO 2006/078781 A1 | 7/2006 |
| WO | WO 2006/078927 A1 | 7/2006 |
| WO | WO 2006088578 A1 | 8/2006 |
| WO | WO 2006/102012 A1 | 9/2006 |
| WO | WO 2006/133311 A2 | 12/2006 |

OTHER PUBLICATIONS

Parodi, J.C., M.D., "Endovascular Repair of Abdominal Aortic Aneurysms," Advances in Vascular Surgery, vol. 1, pp. 85 105 (1993).

Rubino, F. and J. Marescaux, "Effect of Duodenal-Jejunal Exclusion in a Non-obese Animal Model of Type 2 Diabetes, A New Perspective for an Old Disease," Annals of Surgery 239(1):Jan. 1-11, 2004.

Yates III, M. R., et al., "Palliation of Malignant Gastric and Small Intestinal Strictures With Self Expandable Metal Stents," Endoscopy 30:266 272 (1998).

Bethge, N., et al., "Human tissue responses to metal stents implanted in vivo for the palliation of malignant stenoses," Gastrointestinal Endoscopy 43(6):596 602 (1996).

Binkert, C. A., et al., "Benign and Malignant Stenoses of the Stomach and Duodenum: Treatment with Self expanding Metallic Endoprostheses," Radiology 199(2):335 338 (1996).

Cwikiel, W., et al., "Self expanding Stent in the Treatment of Benign Esophageal Strictures: Experimental Study in Pigs and Presentation of Clinical Cases," Radiology 187(3):667 671 (1993).

Dolan, K. et al., "Treating Diabetes in the Morbidly Obese by Laproscopic Gastric Band," Obesity Surgery, vol. 13, pp. 439 443 (2003).

Park, B.P. et al., Malignant Obstruction of Gastric Outlet and Duodenum: Palliation with Flexible Covered Metallic Stents, Radiology 219(3):679 683 (2001).

Dormann, A.J. et al., "Self expanding metallic stents for continous dilatation of benign stenosis in gastrointestinal tract first results of long term follow up in interim stent application in pyloric and colonic obstructions," Z Gastroenteral 39:957 960 (2001).

Pories, W.J., "Why Does the Gastric Bypass Control Type 2 Diabetes Mellitus?" Obesity Surgery, 2:303 313 (1992).

Pories, W.J., et al., "Etiology of Type II Diabetes Mellitus: Role of the Foregut," World J. Surg., 25:527 531 (2001).

Rubino, F., et al., "Potential of Surgery for Curing Type 2 Diabetes Mellitus," Annals of Surgery 236(5): 554 559 (2002).

Sandha, G. S. and Marcon, N. E., "Expandable Metal Stents for Benign Esophageal Obstruction," Gastrointestinal Endoscopy Clinics of North America 9:(3)437 446 (1999).

Feretis, C., et al., "Palliation of Malignant Gastric Outlet Obstruction with Self-Expanding Metal Stents," Endoscopy 28:225-228 (1996).

(56) References Cited

OTHER PUBLICATIONS

CHOOSTENT™, Covered Esophageal Stent, Instructions, Retrieved from the Internet (http://mitech.co.kr/uploads/images/282/use guide esophachoo_english.pdf) on Jul. 26, 2005.

Hwang, J.C., et al., "Covered Retrievable Tracheobronchial Hinged Stent: An Experimental Study in Dogs," *J. Vasc. Interv. Radiol.*, 12(12):1429-1436 (Dec. 2001).

Irie, T., et al., "Relocatable Gianturco Expandable Metallic Stents[1]," *Radiology*, 178:575-578 (1991).

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul. 8, 1995).

Lee, S.H., "The Role of Oesophageal Stenting in the Non-Surgical Management of Oesophageal Strictures," *British J. Radiology*, 74:891-900 (Oct. 2001).

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stent[1]," *Radiology*, 203(3):747-752 (Jun. 1997).

Song, H.Y., et al., "Covered Retrievable Expandable Nitinol Stents in Patients with Benign Esophageal Strictures: Initial Experience[1]," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Yoon, C.J., et al., "Removal of Retrievable Esophageal and Gastrointestinal Stents: Experience in 113 Patients," *American J. of Roentgenology*, 183:1437-1444 (Nov. 2004).

* cited by examiner

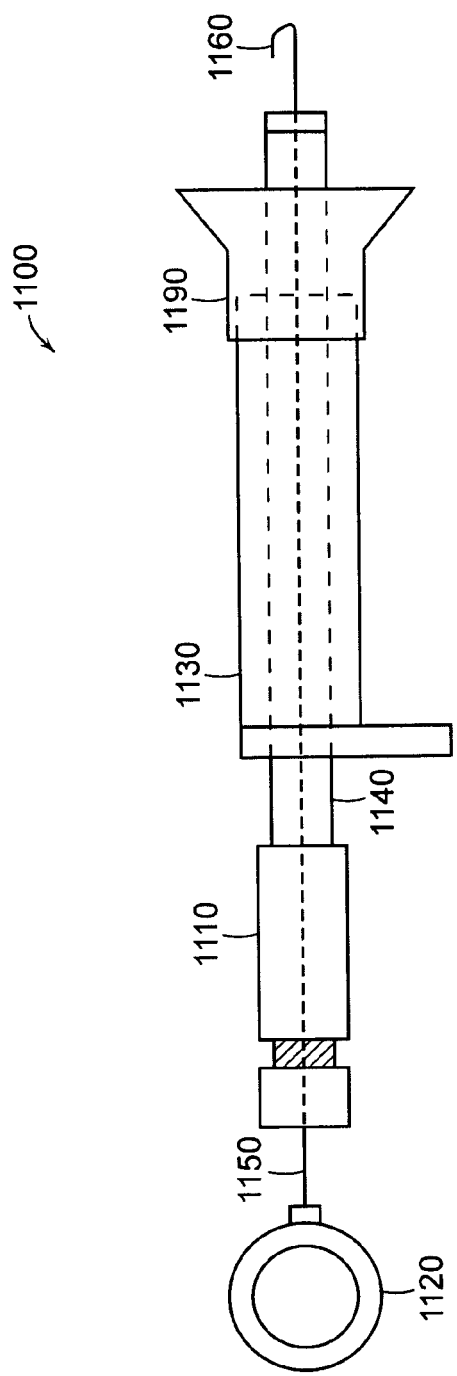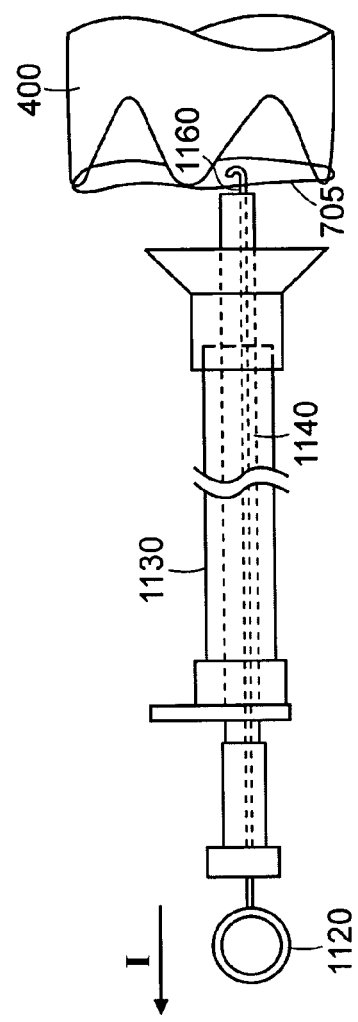

USE OF A GASTROINTESTINAL SLEEVE TO TREAT BARIATRIC SURGERY FISTULAS AND LEAKS

RELATED APPLICATIONS

This application claims the benefit of U.S. Provisional Application No. 60/902,705, filed on Feb. 22, 2007, and U.S. Provisional Application No. 61/005,437, filed on Dec. 5, 2007. The entire teachings of the above applications are incorporated herein by reference.

BACKGROUND OF THE INVENTION

A fistula is an abnormal connection between organs. The rate of occurrence of leaks and fistulas following bariatric surgery ranges from 0.5% to 5%. These occur at staple lines in the gastric pouch or gastrojejunostomy in gastric bypass patients. Despite their relatively low incidence, leaks through fistulas can be life threatening and costly due to increased hospital stays and the need for antibiotics and parenteral nutrition. Regardless of its origin, pouch or gastrojejunostomy, fistulas can reach the skin (gastro- or enterocutaneous), the peritoneal cavity (abscess or peritonitis), adjacent stomach or bowel (gastro-gastric or gastro-enteric), and even the thorax and mediastinum.

The conventional treatment for relatively benign leaks is Nothing Per Oral (NPO) with parenteral nutritional support until the leak or fistula heals. If there is concurrent infection and sepsis, re-operation to suture, drain and gain enteral nutrition access may also be needed.

Experimental endoscopic approaches are being tried to close these leaks. These methods to close the fistula include fibrin glue, endoclips and packing the fistula with various biomaterials. These approaches result in successful healing in up to 70% of the cases, but they require at least three procedures per patient. Less severe gastro-enterostomy leaks and fistulas generally heal without intervention or with one endoscopic treatment. Gastric pouch fistulas are more difficult to close as surgical attempts generally fail.

FIG. 1 is a sectional view of a portion of the digestive tract in a body. Food to be digested enters the stomach 102 through the cardiac orifice 110 from the esophagus 120. The esophagus 120 is a tube that connects the pharynx (not shown) with the stomach 102. In an adult, the esophagus 120 may be about 10 inches long (250 mm). When a person swallows, the muscular walls of the esophagus contract to push food down into the stomach 120. Glands in the lining of the esophagus produce mucus, which keeps the passageway moist and facilitates swallowing. The Gastroesophageal (GE) Junction 122 has two sides, the esophageal side and the gastric side. The Lower Esophageal Sphincter (LES)) encircles the esophagus at the GE Junction 122 and is normally contracted to close the esophagus 120. When the GE Junction 122 closes, the contents of the stomach 102 cannot flow back into the esophagus 120.

Chyme, a semi-fluid, homogeneous creamy or gruel-like material produced by gastric digestion in the stomach exits the stomach through the pyloric orifice (pylorus) 108 and enters the small intestine 112. The pylorus 108 is a distal aperture of the stomach 102 surrounded by a strong band of circular muscle. The small intestine, about nine feet in length, is a convoluted tube, extending from the pylorus to the ileocaecal valve where it terminates in the large intestine. The small intestine 128 has three sections, the duodenum 104, the jejunum 106 and the ileum (not shown). The first eight- to ten-inch section of the small intestine 128, the duodenum, is the shortest, widest and most fixed part of the small intestine.

The duodenum 104 has four sections: superior, descending, transverse and ascending which typically form a U-shape. The superior section is about two inches long and ends at the neck of the gall bladder. The descending section is about three to four inches long and includes a nipple shaped structure (papilla of vater) 114 through which pancreatic juice from the pancreas and bile produced by the liver and stored by the gall bladder enter the duodenum from the pancreatic duct. The pancreatic juice contains enzymes essential to protein digestion, and bile dissolves the products of fat digestion. The ascending section is about two inches long (50.8 mm) and forms the duodenal-jejunal flexure 116 where it joins the jejunum 106, the next section of the small intestine. The duodenal-jejunal flexure 116 is fixed to the ligament of Treitz 118 (musculus supensionus duodeni). The juices secreted in the duodenum break the partially digested food down into particles small enough to be absorbed by the body. The digestive system is described in Gray's Anatomy ("Anatomy of the Human Body", by Henry Gray) and "Human Physiology", Vander, $3^{rd}$ ed., McGraw Hill, 1980, the contents of which are incorporated herein by reference in their entireties.

Gastric bypass surgery makes the stomach smaller and allows food to bypass part of the small intestine. A person will feel full more quickly than when the stomach was its original size, which reduces the amount of food one can eat and thus the calories consumed. Bypassing part of the intestine also results in fewer calories being absorbed. This leads to weight loss. The most common gastric bypass surgery is a Roux-en-Y gastric bypass. FIG. 2A is a sectional view of one surgical approach to a Roux-en-Y gastric bypass procedure. In this procedure, the surgeon first divides the stomach and creates a small stomach pouch 202 using staples 206, and then constructs a "bypass" for food. The small pouch 202 is about 40 to 60 cc. The bypass allows food to skip parts of the small intestine 128. By skipping a large part of the small intestine 128, the body cannot absorb as many calories or nutrients.

To make the bypass, the surgeon then makes a cut about one foot below the stomach 102 (Points A and B), which may be in the jejunum 106. Then a new 0.5 inch (15 mm) opening (stoma) is created in the small stomach pouch 202 (Point C). Referring to FIG. 2B, the surgeon then attaches the open end of the small intestine (Point B) to the new opening at Point C, creating a Roux limb 208. The Roux limb 208 carries food and fluids from the stomach pouch 202 into the lower portion of the small intestine 128.

The remaining end at Point A is stapled to close the opening. A new opening is created at Point D. The surgeon attaches Point A' to the new opening at Point D, creating a "Y-shaped" or "Y-limb" intestinal junction 210. The Y-limb carries digestive juices from the bypassed stomach, pancreas, liver, and duodenum to the remaining intestines. The opening is made at Point D to allow digestive juices to flow into the lower portion of the small intestine 128.

Although the Roux-en-Y Procedure is an effective weight loss procedure, there are risks associated with such a procedure. For example, fistulas 205 and leaks can occur at the staple linings 206 and more typically at the stoma (Point B to C). Attempts have been made to treat these fistulas and leaks surgically and by covering them with stents that were typically designed to open strictures. For example, the Ultraflex™ Esophageal NG Stent System and Polyflex™ stents by Boston Scientific Corporation and the stents by Cook® Medical Incorporated, as well as the Choo stent (for example as in the Journal article by Steimann, R. U.; Zundler, J.; Kreichgauer, H. P.; Bode, J. C. (2000). A new stent device (Choo stent) for palliation of malignant gastric outlet obstruction. *Endoscopy*, 32 (5)) have been used to cover fistulas and/or leaks.

SUMMARY OF THE INVENTION

There are problems associated with such use of stents. The stents were designed for permanent long term use rather than temporary use. It is difficult to remove the stents, and they may have open areas that permit tissue in-growth that results in tissue damage with surgical removal.

The stents do not have good position stability when positioned to cover a fistula. The stents were designed to be mounted over or well above the GE Junction, so when the practitioner moves the stent down the esophagus to cover the fistulas and/or leaks, these stents lose stability and frequently migrate.

Further, due to the rigidity of the stents, the stents dilate the fistulas and/or leaks thereby causing irritation and ischemic pressure on the fistulas and/or leaks. The dilation of the anastomosis also counters the goal of having a restricted passageway from the stomach to the intestine for weight loss.

The present invention provides a method for treating a Roux-en-Y patient having fistulas and/or leaks as a result of bariatric surgery. A gastrointestinal implant device is anchored in the esophagus. The implant may include an anchor coupled to a proximal portion of a flexible, floppy sleeve, open at both ends and unsupported at a distal portion extending beyond the anchor. The flexible, floppy sleeve is extended through a stomach pouch into an intestine anastomosed to the stomach pouch. The sleeve prevents or shields fistulas and leaks from making contact with food and/or fluids.

The length of the sleeve can be varied, but at least extends through the stomach pouch into an intestine joined to the stomach pouch. In some embodiments, the sleeve extends into the jejunum.

The flexible, floppy sleeve imposes no outward pressure on the fistula, leak, or anastomosis. Advantageously, the material of the sleeve is slippery so as not to irritate the fistulas and/or leaks, thereby allowing the fistulas and/or leaks to heal. In preferred embodiments, the sleeve material has a coefficient of friction of less than about 0.2. The sleeve may be formed of a biocompatible, low-friction material such as a fluoropolymer. Preferably, the sleeve is formed of expanded polytetrafluoroethylene (ePTFE). Additionally, the sleeve may be coated or impregnated with a second material, such as Teflon® Fluorinated Ethylene Propylene (FEP), polyurethane, or silicone to reduce permeability. Still further, the distal end of the sleeve may be directionally textured.

The anchor may be collapsible for ease of insertion and/or removal. For example, the anchor may be inserted and/or removed endoluminally using a catheter-based procedure. The collapsible anchor is also well adapted for retention in the esophagus, being capable of collapsing and/or flexing in response to natural movements of the local anatomy. The anchor can be covered by a membrane, such as a proximal portion of the sleeve, and in some embodiments is sandwiched between a first inner layer of membrane and a second outer layer of membrane.

In another aspect, the anchor is a stent. Preferably the stent is a wave anchor. The wave anchor includes a compliant, radial spring shaped into an annular wave pattern about a central axis, providing an outward radial force, while allowing substantial flexure about its perimeter. Such flexure is advantageous as it allows for minimally-invasive delivery and ensures that the device will substantially conform to the surrounding anatomical structure when implanted. The annular wave element can be formed from one or more elongated resilient members and defines a lumen along its central axis formed between two open ends. When implanted, the central axis of the anchor is substantially aligned with the central axis of the esophagus, allowing food and fluids to pass through the device. Additionally, the compliant wave anchor minimizes trauma to the tissue by providing sufficient flexibility and compliance, while minimizing the likelihood of tissue erosion and providing a solid anchoring point to the tissue.

When implanted, the anchor enables a sleeve to be securely implanted within the esophagus, preferably providing a fluid seal at the proximal end. To enhance a fluid seal, the proximal end of the sleeve can be contoured along a leading edge of the wave anchor. Thus, food and fluids are allowed to flow substantially unimpeded into the sleeve without becoming entrapped at the anchor.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 11 is a schematic diagram showing an exemplary embodiment of the invention repositioning device; and FIG. 12 is a schematic diagram showing an exemplary embodiment of the invention capturing a proximal portion of an implantable device.

DETAILED DESCRIPTION OF THE INVENTION

A description of preferred embodiments of the invention follows.

A fistula is an abnormal connection between organs. Fistulas and leaks can occur as a result of bariatric surgery, in particular after a Roux-en-Y gastric bypass procedure. A gastrointestinal implant device is anchored in the esophagus and extends through a stomach pouch into an intestine anastomosed to the stomach pouch to prevent fistulas and other damaged tissue from making contact with food and/or fluids entering the esophagus, thus enabling healing of the damaged tissue.

Figure 3:
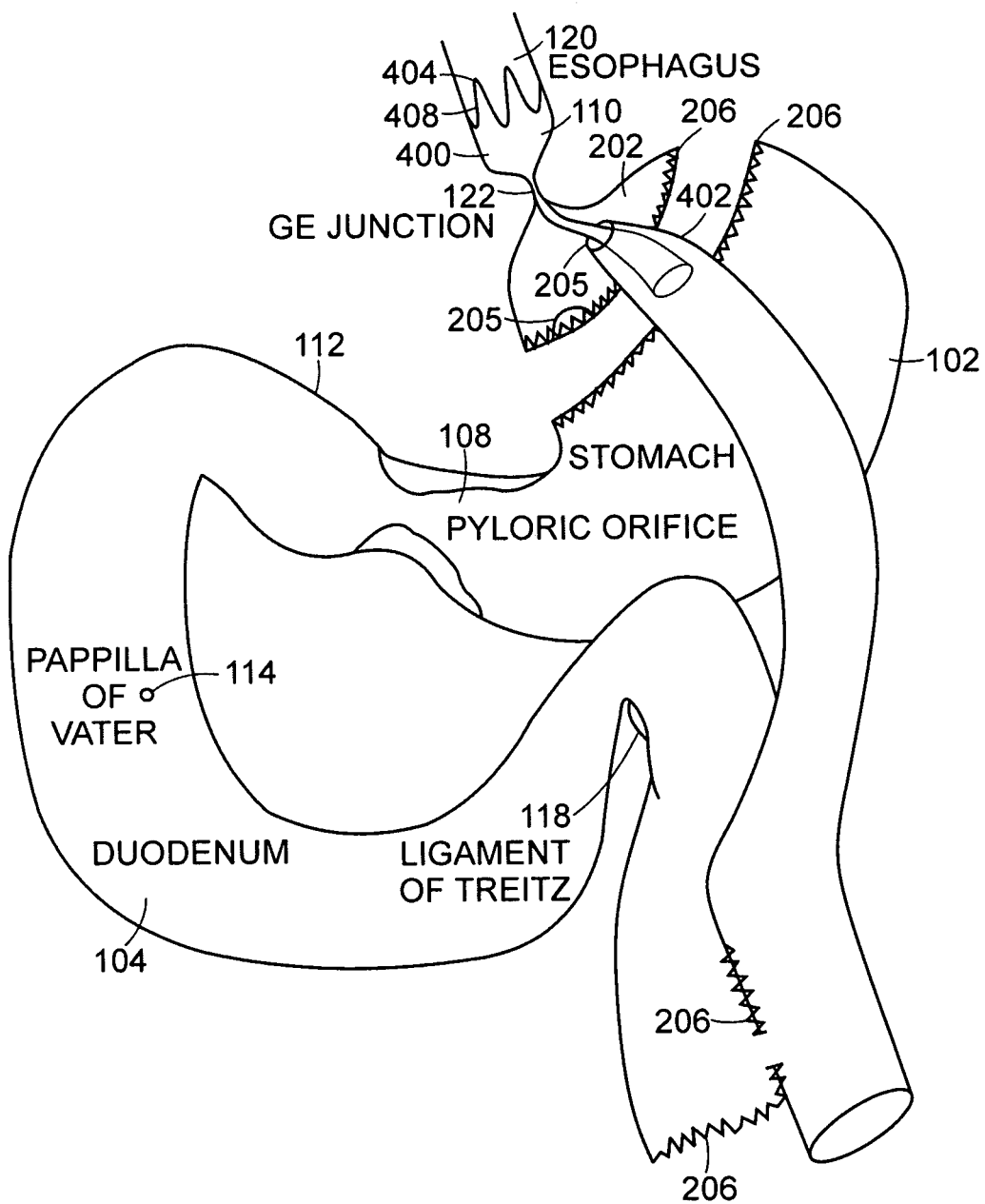
FIG. 3 is a sectional view of a body showing one embodiment of the gastrointestinal implant device implanted in the esophagus of a Roux-en-Y patient.

FIG. 3 is a sectional view of a body showing one embodiment of the gastrointestinal implant device 400 implanted in the esophagus, preferably just above the GE Junction 122. The device 400 includes an anchor and a sleeve. The anchor may have drawstrings to facilitate the removal of the implant device 400. The anchor has a relaxed diameter of 0.7-1.5 inches (20-40 mm). The sleeve attached to the anchor may be at least 6 inches (150 mm) long to pass from the esophagus, over the fistulas and/or leaks, and through the small pouch into an intestine anastomosed to the small pouch.

The gastrointestinal implant device has little or no tissue adhesion into the anchor or sleeve. Moreover, retrieval sutures (or drawstrings) make removal simple which is important for temporary usage until the fistulas and/or leaks heal. The sleeve extends over the leak and/or fistula area, preventing food and saliva from contacting the area without putting compression on the area. Further, the flexible floppy sleeve has no hoop strength, so that it can fall flat until food and/or fluids pass through. The lack of hoop strength allows the sleeve to collapse with no resistance to any applied inward force and itself imposes no outward dilating force. In this way, the sleeve allows the fistula and/or leaks to heal without ischemic pressure from an internal device.

The first proximal end 404 (FIG. 4) of the implant device 400 (FIG. 4) is anchored just above the GE Junction 122 of the esophagus 120. The stent 408 (FIG. 4) is collapsible and has a diameter that is larger than the diameter of the GE Junction 122. The diameter of the stent 408 (FIG. 4) has a relaxed diameter within the range of 0.7-1.5 inches (20-40 mm). As a result, the stent 408 (FIG. 4) has good positional stability because the radial outward force abuts the muscle of the esophagus 120. This in combination with the longitudinal support by the GE Junction 122 anchors the implant device 400 (FIG. 4) in place so that the implant device 400 can not be dragged into the small stomach pouch 202 or down into the Roux limb 208 and intestines with movement of the stomach pouch and the intestines. The small stomach pouch lacks the very strong peristaltic action of a normal stomach that would pull the anchor loose. The GE Junction 122 may continue to normally contract to prevent contents of the stomach 102 to flow back into the esophagus 120. The sleeve 402 (FIG. 4) extends into the Roux limb 208 and may extend beyond the proximal jejunum 106.

Figure 4:
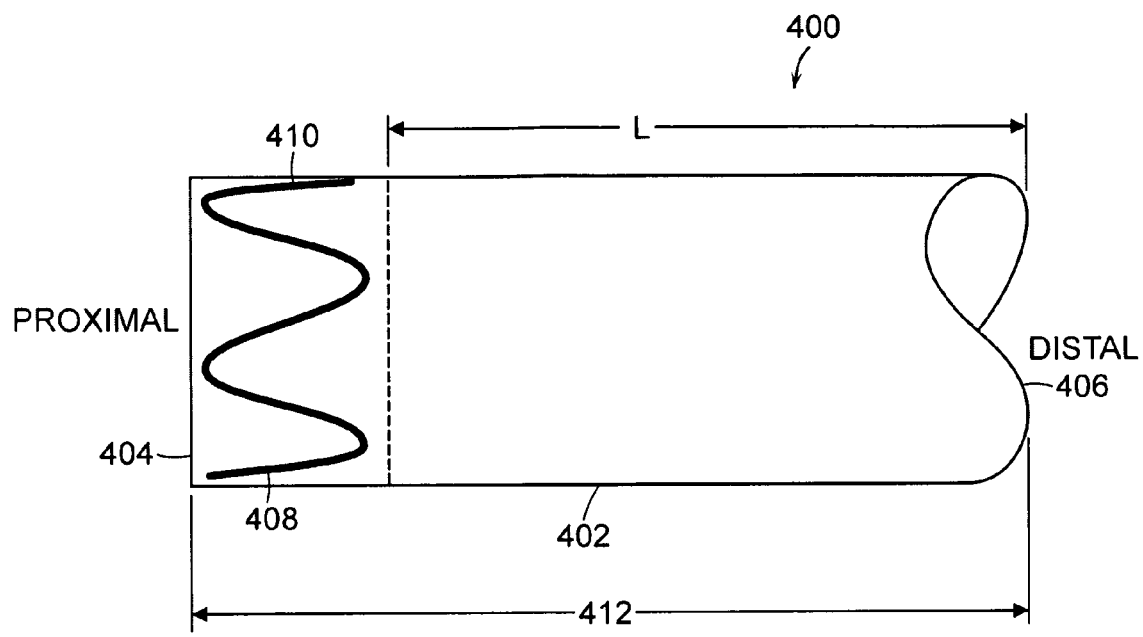
FIG. 4 is a perspective view of a gastrointestinal implant device according to the principles of the present invention.

After the gastrointestinal implant device 400 (FIG. 4) has been placed in the body and anchored just above the GE Junction 122 of the esophagus 120, food and fluids entering the esophagus 120 (FIG. 1) passes through passageway 404 (FIG. 4) inside the sleeve 402 (FIG. 4). By directing the food and fluids through the sleeve 402 any fistulas and/or leaks on the way and in particular at the stoma (Point B to C of FIG. 2B) will be prevented from making contacts with food and fluids, thereby allowing the fistulas and/or leaks to heal. The slippery, flexible, floppy sleeve 402 (FIG. 4) is able to go through the stoma without causing ischemic pressure and/or irritation to the fistulas 205 and/or leaks.

Figure 1:
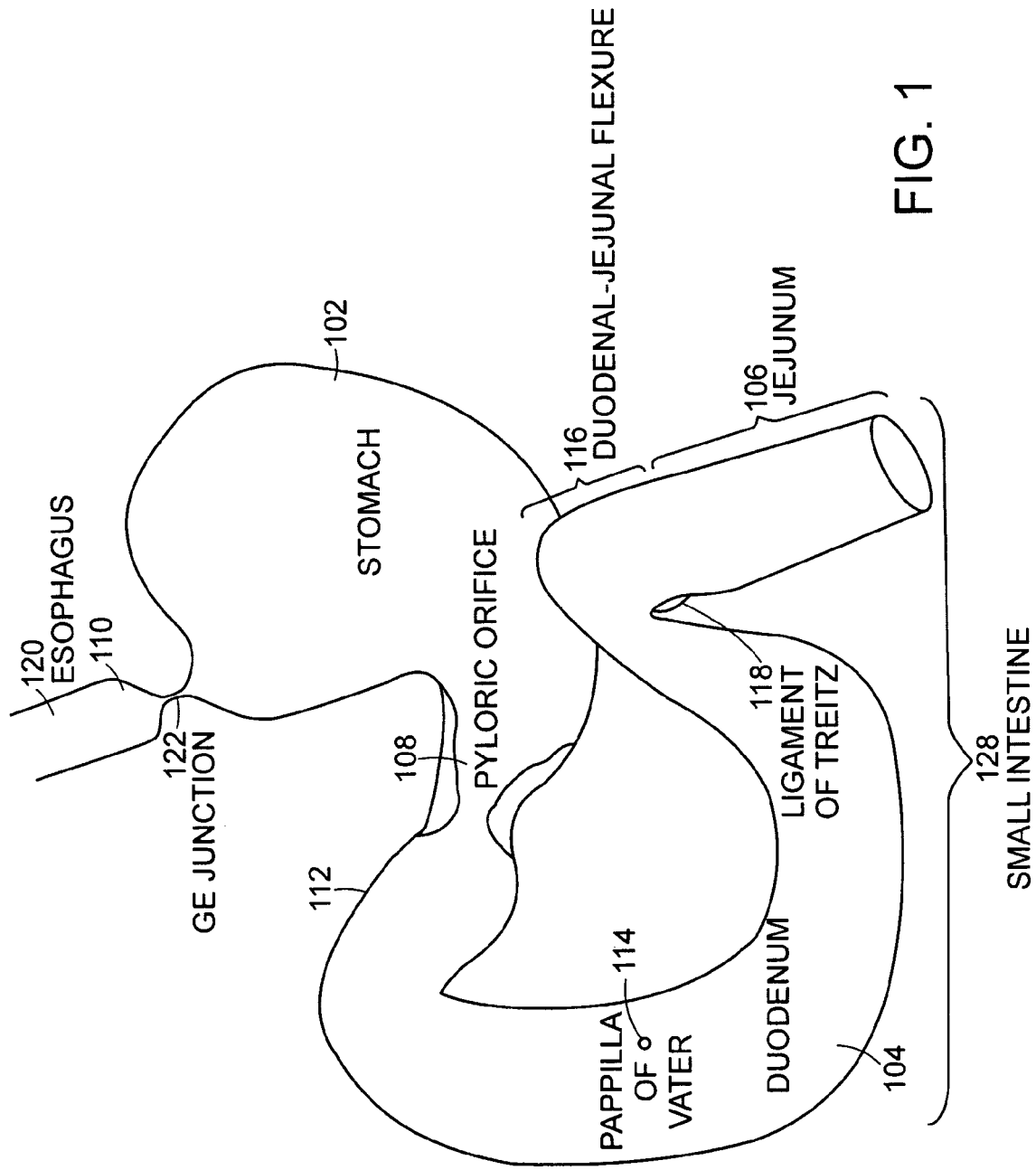
FIG. 1 is a sectional view of a portion of the digestive tract in a body.

FIG. 4 is a perspective view of a gastrointestinal implant device 400 according to the principles of the present invention. The gastrointestinal implant device 400 includes an elongated open-ended flexible sleeve 402 having a first proximal opening 404 and a distal opening 406. Within the sleeve 402 is a passageway that extends from the first proximal opening 404 to the second distal opening 406 for transporting the food (typically liquid food) and fluids entering the esophagus 120 (FIG. 1). The surface of the passageway (the interior surface of the implant device 400) is smooth to enable the food and fluids to easily pass through. The exterior surface of the implant device 400 is smooth to prevent tissue ingrowth and to be non-irritating to the esophagus. In one embodiment, the length L of the flexible, floppy sleeve 402 is selected to extend through the small stomach pouch 202 (FIG. 2A) into an intestine anastomosed to the stomach pouch 202 (FIG. 2A) and covering any fistulas 205 (FIG. 2B) and/or leaks.

Within the implant device 400, at the proximal end including the first proximal opening 404, is a collapsible self-expanding anchor 408. The diameter of the anchor 408 is dependent on the diameter of the gastroesophageal (GE) Junction 122 (FIG. 1) and is in the range of about 0.7-1.5 inches (20-40 mm) based on human anatomy variations, typically about 25 mm. The anchor 408 may be a collapsible self-expanding stent.

The sleeve 402 material is thin and conformable so that it collapses in the intestine to a small volume to minimize esophagus irritability. It has a low coefficient of friction (<0.20) so that food and fluids slide easily through it and the esophagus slides easily around it. It is of low permeability to fluids so that the food and fluids do not touch the esophagus wall. It is biologically inert and non-irritating to the tissues. One such material is expanded polytetrafluoroethylene (ePTFE), a fluoropolymer, with a wall thickness of about 0.0005-0.001 inches (0.012-0.025 mm) and an internodal distance of 20 microns. This material is hydrophobic but is slightly porous. However, these very small pores may plug over time. The porosity may be reduced by coating the material on the inside, outside or in the pores with dilute solutions, such as Teflon®Fluorinated Ethylene Propylene (FEP), silicone, or polyurethane. Another material is polyethylene with a wall thickness of less than 0.001 inches (0.025 mm). Rubber-like materials typically have friction coefficients of 1-4, significantly stickier than these materials. However, in alternate embodiments other materials having similar characteristics can be used.

Figure 2A:
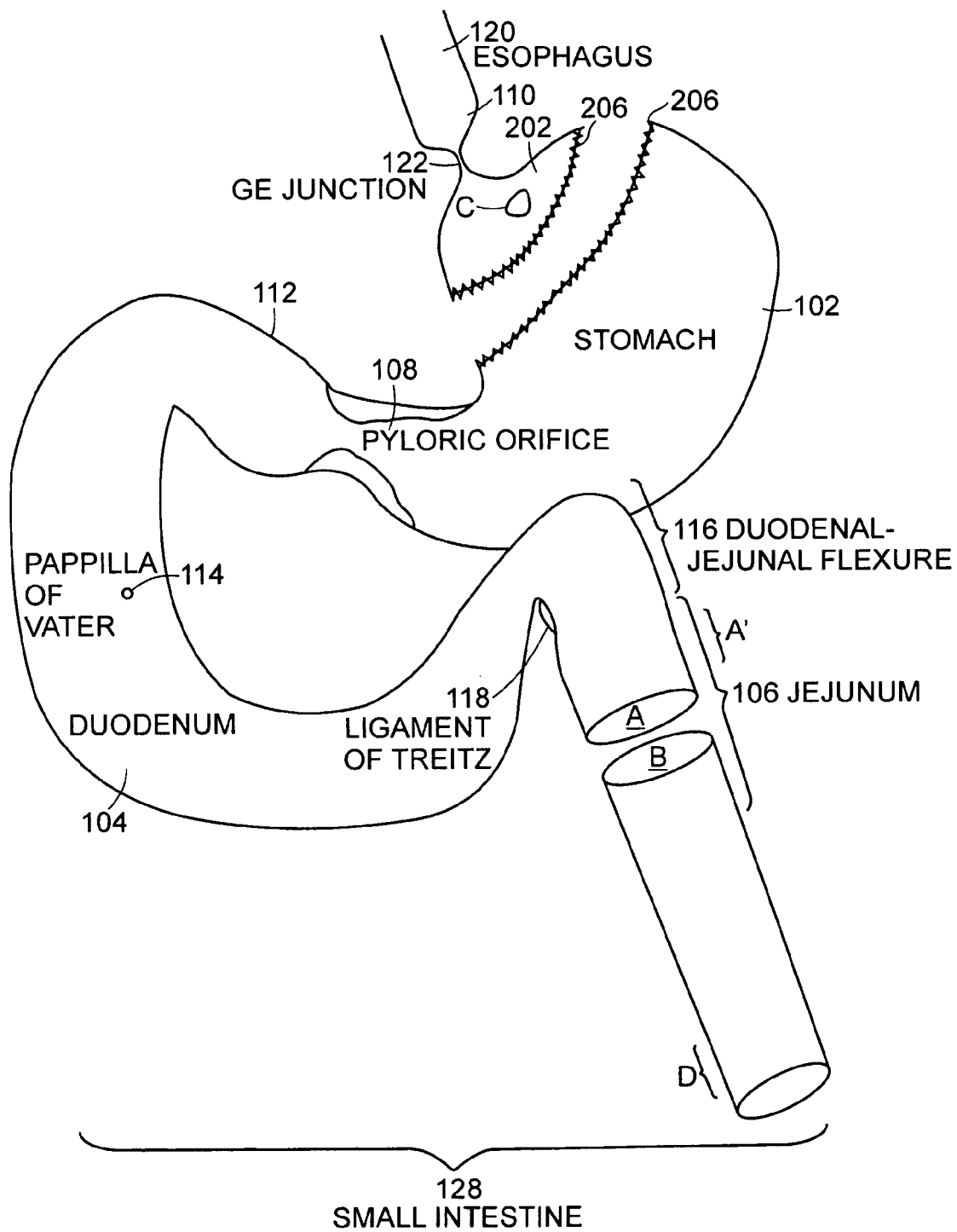
FIGS. 2A-2B are sectional views of a Roux-en-Y gastric bypass procedure.
Figure 2B:
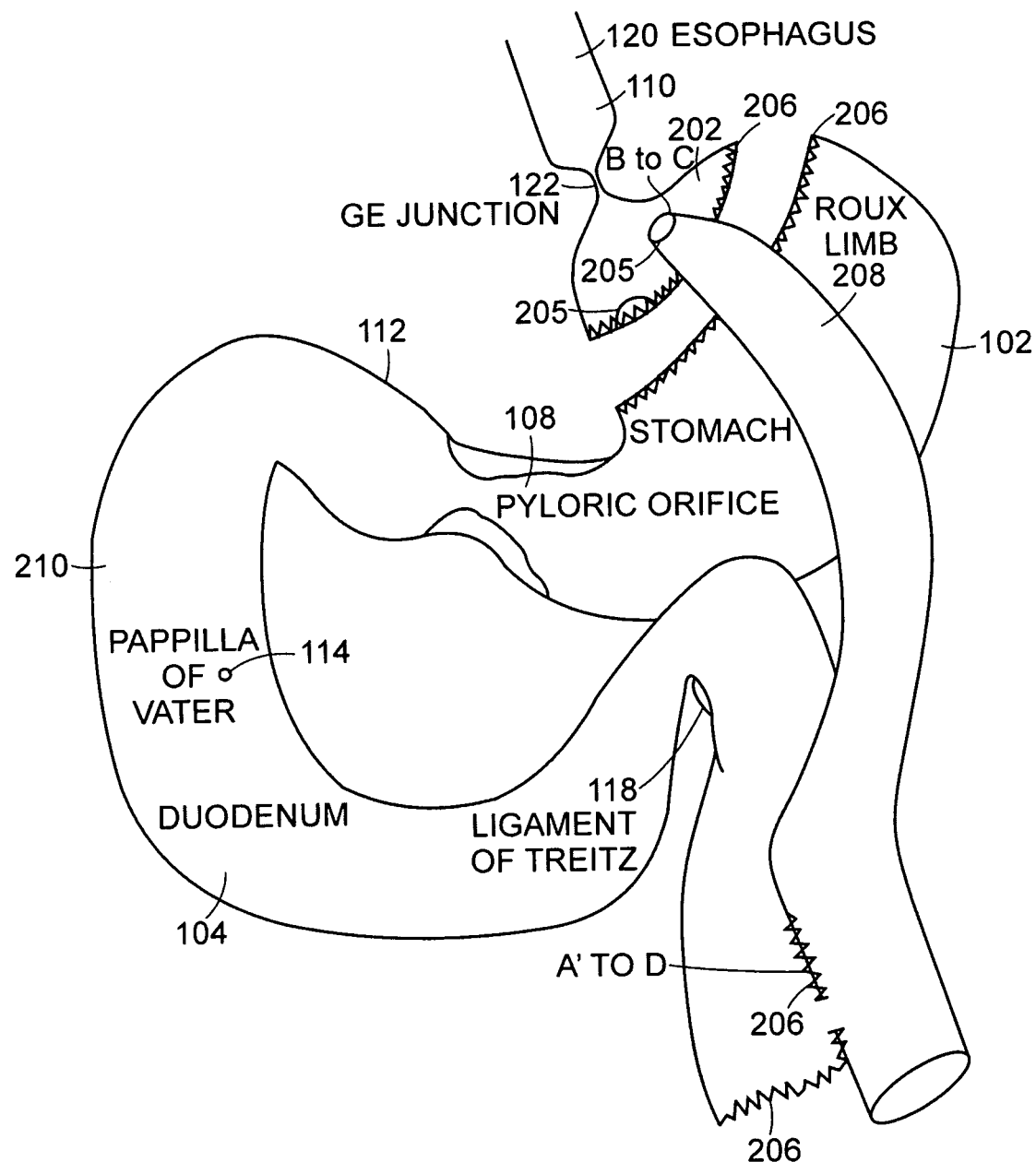

The overall length 412 of the sleeve 402, including the anchor is at least long enough to go through the small stomach pouch 202 (FIG. 2A). To that end, the overall length 412 may be at least 6.0 inches (150 mm). A longer sleeve 402, for example, greater than one foot (30 cm), may extend down through the Roux limb 208 (FIG. 2B) into the jejunum 106 (FIG. 1). The length 412 of the sleeve 402 may be selected to bypass a portion of the jejunum 106.

Markings can be added to the exterior surface of the sleeve 402 to detect the position and orientation of the sleeve on a fluoroscopic image and whether the sleeve is twisted. For example, a stripe can be painted down the length of the device 400 using tantalum impregnated ink, or tantalum bands can be bonded to the exterior surface of the device.

For more details regarding the sleeve, reference U.S. Pat. No. 7,267,694 filed Nov. 30, 2004, entitled "Bariatric sleeve," which is hereby incorporated by reference in its entirety. The sleeve as cited in the above reference is anchored in the intestine and has different diameter and length than discussed in this application. Further, the cited reference includes barbs; however, in this application, preferably no barbs are required to anchor the implant in the esophagus.

Figure 5:
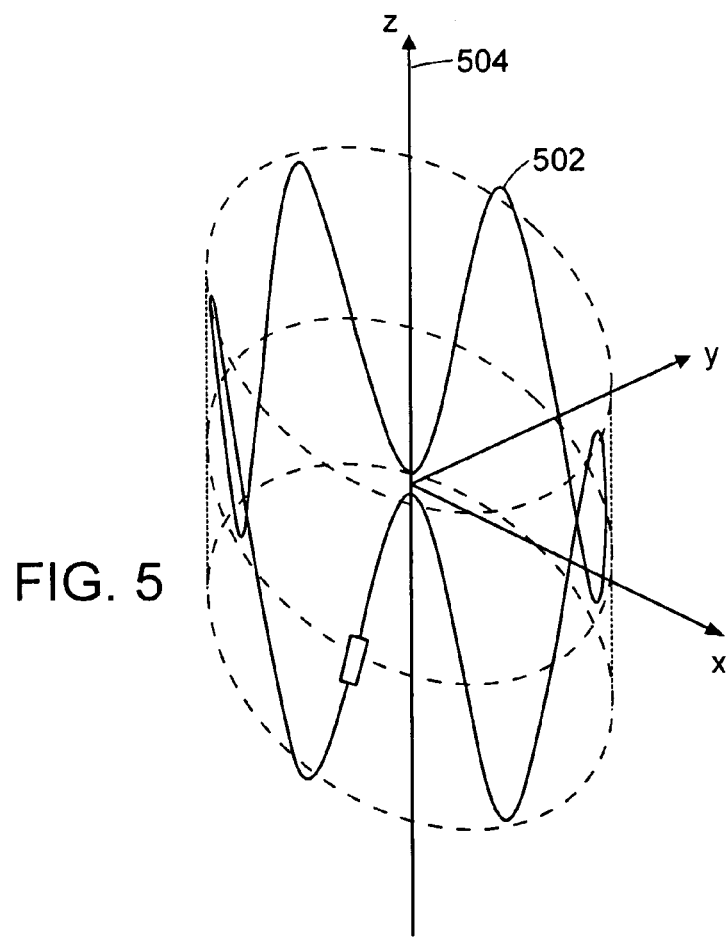
FIG. 5 is a more-detailed perspective view of the anchoring device of FIG. 4.

The implant device 400 may include a wave anchor 410 coupled to a proximal portion 404 of the sleeve 402. Referring to FIG. 5, the wave anchor 410 includes a compliant, radial spring 502 shaped into an annular wave pattern about a central axis 504, providing an outward radial force, while allowing substantial flexure about its perimeter. Such flexure is advantageous as it allows for minimally-invasive delivery and ensures that the device will substantially conform to the surrounding anatomical structure when implanted. The annular wave element 502 can be formed from one or more elongated resilient members and defines a lumen along its central axis formed between two open ends. When implanted, as shown in FIG. 3, the central axis of the anchor 410 is substantially aligned with the central axis of the esophagus 120, allowing food and fluids to pass through the device 400. Additionally, the compliant wave anchor 410 minimizes trauma to the tissue by providing sufficient flexibility and compliance, while minimizing the likelihood of tissue erosion and providing a solid anchoring point to the tissue of the GE Junction 122. For more details regarding the compliant wave anchor 410, reference U.S. patent application Ser. No. 11/147,992 filed Jun. 8, 2005, entitled "Gastrointestinal Anchor Compliance" and U.S. patent application Ser. No. 10/858,851 filed Jun. 1, 2004, entitled "Intestinal Sleeve," which are hereby incorporated by reference in their entireties. The sleeve as cited in the above references has different diameter and length than discussed in this application. Further, the cited references include barbs; however, in this application, preferably no barbs are required to anchor the implant in the esophagus.

The compliant wave anchor 410 can be manufactured from a resilient metal such as a heat-treated spring steel, stainless steel, or from an alloy such as NiTi alloy commonly referred to as Nitinol. Other alloys include nickel-cobalt-chromium-molybdenum alloys possessing a unique combination of ultrahigh tensile strength, such as MP35N. Additionally, the wave anchor 410 can be formed from a polymer and/or a composite having similar properties. The wave anchor 410 can be manufactured from a single strand, such as a wire, contoured into the desired shape. Alternatively, the wave anchor 410 can be manufactured from multi-strands of the same or different materials similarly contoured to the desired shape. In some embodiments, the wave anchor 410 can be cut into the wave shape from tubular stock of the desired material, such as Nitinol.

Figure 6:
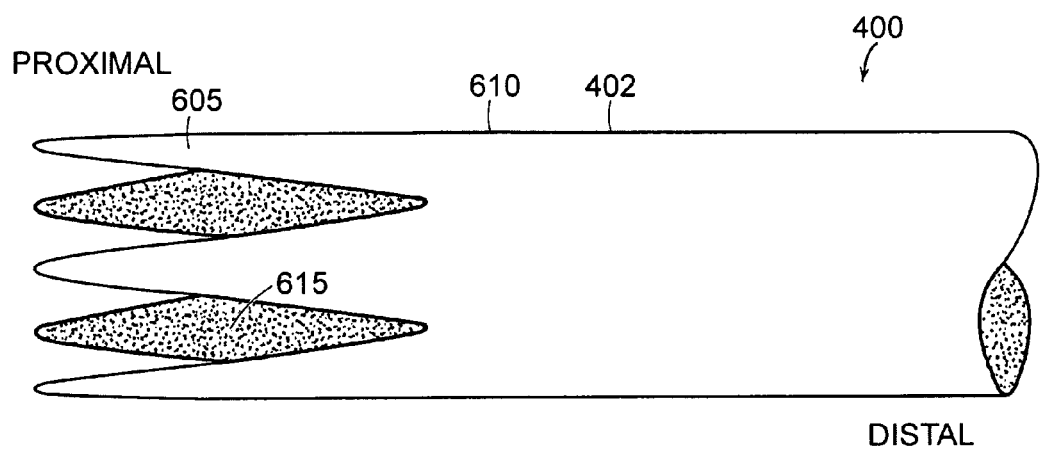
FIG. 6 is a perspective view of an alternative embodiment of the gastrointestinal implant device of FIG. 4.

The anchor 410 can be removably attached within the body using any of the methods described herein for securing an anchor, including the possible use of barbs attached to, and/or formed on the anchor itself. Preferably, the anchor 410 is radially collapsible for endoscopic insertion. When implanted, the anchor enables a sleeve, or barrier to be securely implanted within the esophagus 120, preferably providing a fluid seal at the proximal end. To enhance a fluid seal, the proximal end of the sleeve can be contoured to the wave anchor 410 as shown in FIG. 6. For a device 400 using a sleeve 402 contoured to the wave anchor 410, the proximal end appears tulip-shaped.

Continuing with FIG. 6, the wave anchor 408 may be sandwiched between a first outer layer membrane 610 and a second inner layer membrane 615 at the proximal end of the sleeve 402. Preferably the sleeve 402 is an extension of the first outer layer of the membrane 605. The covered exterior surface of the stent 605 prevents tissue growth to allow removal of the implant device 400. The covered interior surface of the stent 605 provides a smooth passageway for food and fluids to bypass part of the jejunum 106. The diameter of the sleeve 402 is selected such that the first outer layer of the membrane 610 fits over the stent 605.

Figure 7:
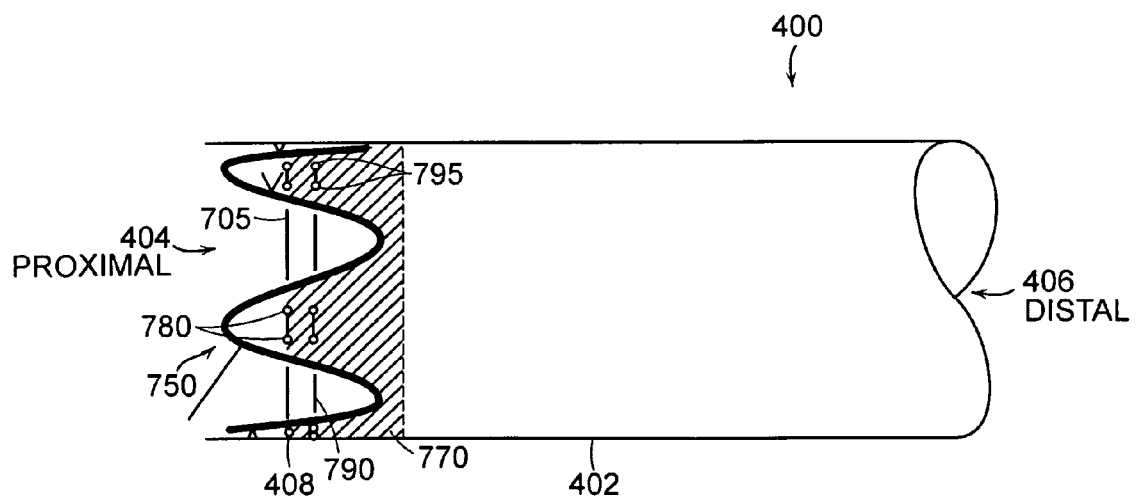
FIG. 7 illustrates an embodiment of a gastrointestinal implant device with a wave anchor and drawstrings.

FIG. 7 illustrates an embodiment of a gastrointestinal device with a wave anchor and drawstrings. The anchor 408 can be configured with a drawstring 705. The drawstring 705 can facilitate repositioning and/or removal of the implant device 400. The drawstring 705 is shown woven through pairs of eyelets 780 distal to the wave peak 750 in the webbing material 770. The implantable device 400 can also include a second drawstring 790 distal to drawstring 705. This drawstring can also be woven through pairs of eyelets 795 distal to eyelets 780 for drawstring 705. The second drawstring 790 is an alternative drawstring in the situation that the first drawstring 705 breaks during repositioning or removal. The drawstring, when pulled, contracts about the perimeter of the anchor 408, thereby reducing the diameter of the anchor 408. Thus, the drawstring can be used to facilitate removal of an implanted anchor 408 by pulling it away from the surrounding anatomy.

Although the preferred embodiments do not need or use barbs for anchoring the implant device 400 just above the GE Junction 122, the anchor 408 may include a plurality of opposing barbs (not shown). The barbs may protrude from the exterior surface of the anchor 408 through the first outer layer of the sleeve 402.

A flexible, anti-rotation, anti-buckling mechanism (not shown) may be attached to the sleeve 402 and extends from below the distal end of the anchor along the length of the sleeve to the distal end of the sleeve 406. For more details regarding the anti-buckling mechanism, reference U.S. patent application Ser. No. 10/858,851 filed Jun. 1, 2004, entitled "Intestinal Sleeve" and U.S. patent application Ser. No. 11/494,284 filed Jul. 27, 2006, entitled "Anti-buckling sleeve," which are hereby incorporated by reference in their entireties.

Figure 8:
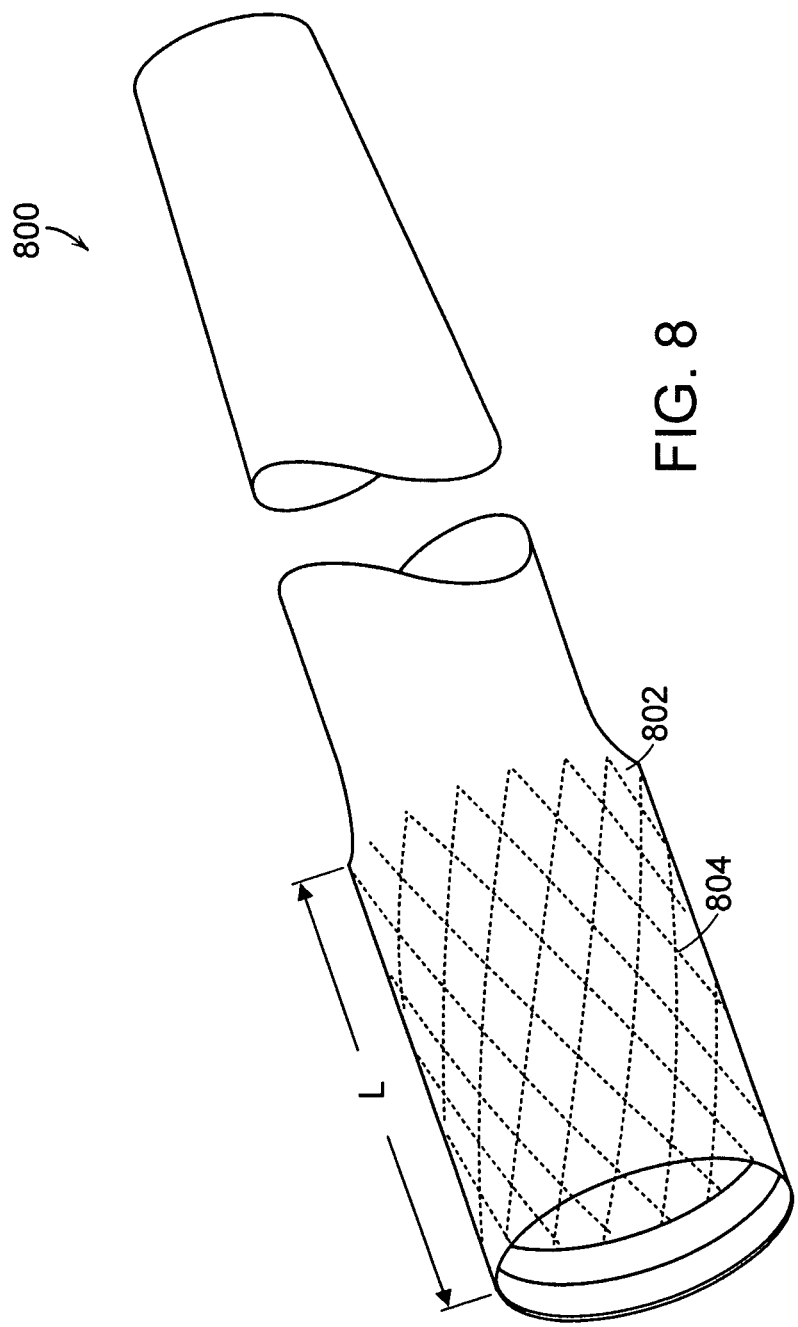
FIG. 8 is a perspective view of a gastrointestinal implant device with another embodiment of an anchoring device.

FIG. 8 is a perspective view of a gastrointestinal implant device 800 with another embodiment of a collapsible self-expanding stent anchoring device. The anchor 802 includes a plurality of flat struts 804 forming an open space pattern to ease collapsing while ensuring self-expansion. The open space pattern allows for collapsing into a catheter for endoscopic delivery and removal. The struts 804 may be manufactured from heat-treated spring steel such as Nitinol or MP35N.

In the embodiment shown, the anchor 802 has a length L of about 0.9-1.5 inches (25-40 mm) and has a relaxed diameter D of 0.7-1.5 inches (20-40 mm). The struts 804 are flat, about 0.010 inches wide (0.2 mm) and about 0.004-0.010 inches (0.1 to 0.2 mm) thick. The anchor can be formed from a tube of material by laser cutting followed by expansion and heat setting, or other methods well known to those skilled in the art.

In an alternate embodiment, the struts 804 can be formed separately and the strut intersections can be welded or attached by other means well known to those skilled in the art.

Figure 9:
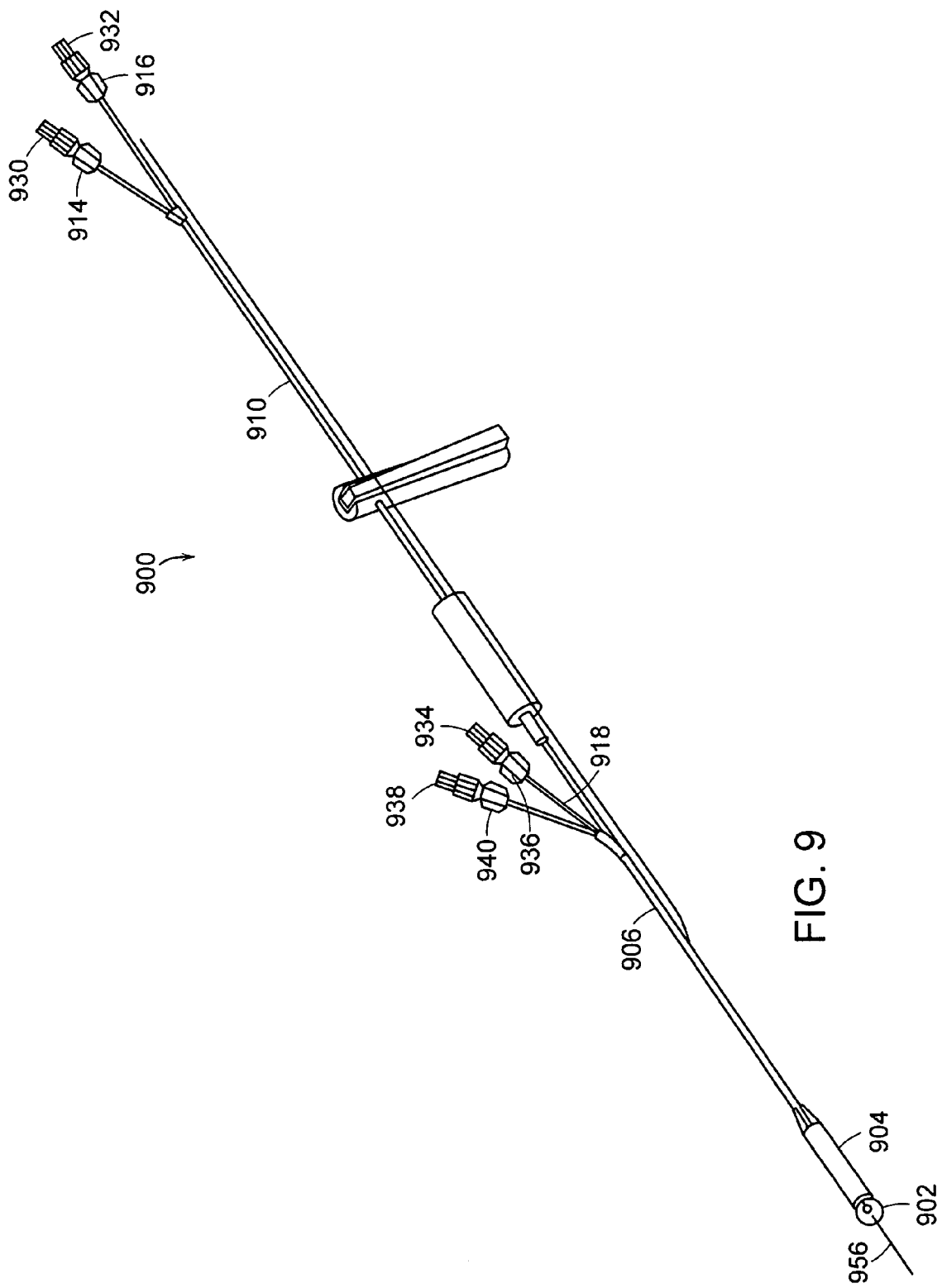
FIG. 9 is a schematic view of an assembled delivery catheter system for delivery of the gastrointestinal implant device.

FIG. 9 is a schematic view of an assembled delivery catheter system for delivery of the gastrointestinal implant device of 400, 800. Typically, the sleeve and anchor are delivered transorally through the mouth. As shown in FIG. 9, delivery catheter system 900 includes an atraumatic tip comprising atraumatic ball 902, a container assembly that includes capsule or container 904, outer catheter 906, and inner catheter 910. Inner and outer catheters 910, 906 and container 904 are made from materials commonly used to form catheters. For example, inner catheter 910 can be made of a polyether block amide (e.g., Pebax® 7233, available from Arkema Group, Paris, France). In some embodiments, outer catheter 906 is made of high density polyethylene and/or container 904 is made of hard plastic (e.g., acetal or polycarbonate). Preferably, catheters 910, 906 are made from materials having frictional properties that facilitate the movement of catheter 910 relative to catheter 906 and facilitate the movement of inner catheter 910 and container 904 in the gastrointestinal tract. System 900 includes ball locking wire knob 930 and stiffening wire knob 932. Ball locking wire knob 930 extends from ball locking wire port 914 to distal end 902 via ball locking wire lumen (not shown) defined by inner catheter 910. Stiffening wire knob 932 extends from stiffening wire port 916 to distal end 902 via stiffening wire lumen (not shown) defined by inner catheter 910.

System 900 includes anchor locking wire 934, a means for displacing an anchor from the container assembly that includes anchor plunger 938, and guidewire 956. Anchor locking wire 934 extends from anchor locking wire port 936 to container 904 via anchor locking wire lumen (not shown) defined by outer catheter 906. Anchor plunger 938 extends from anchor plunger port 940 to container 904 via anchor plunger lumen (not shown) defined by outer catheter 906.

For more details regarding the catheter system for the delivery of the gastrointestinal implant devices 400, 800, reference U.S. patent application Ser. No. 11/057,861 filed Feb. 14, 2005, entitled "Methods and devices for placing a gastrointestinal sleeve," which is hereby incorporated by reference in its entirety.

Figure 10A:
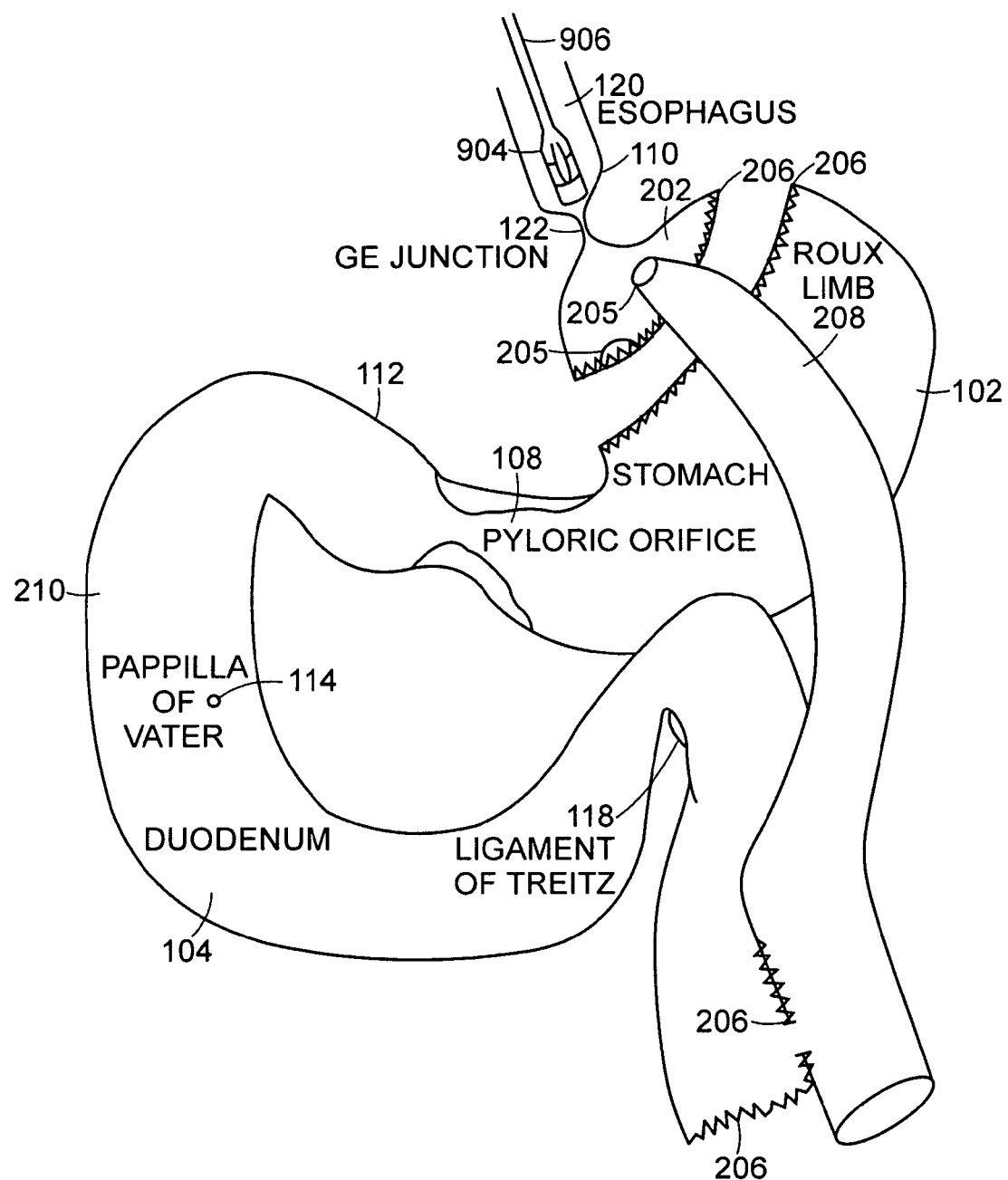
FIGS. 10A-10B are snapshot diagrams illustrating the placement of the gastrointestinal implant device.
Figure 10B:
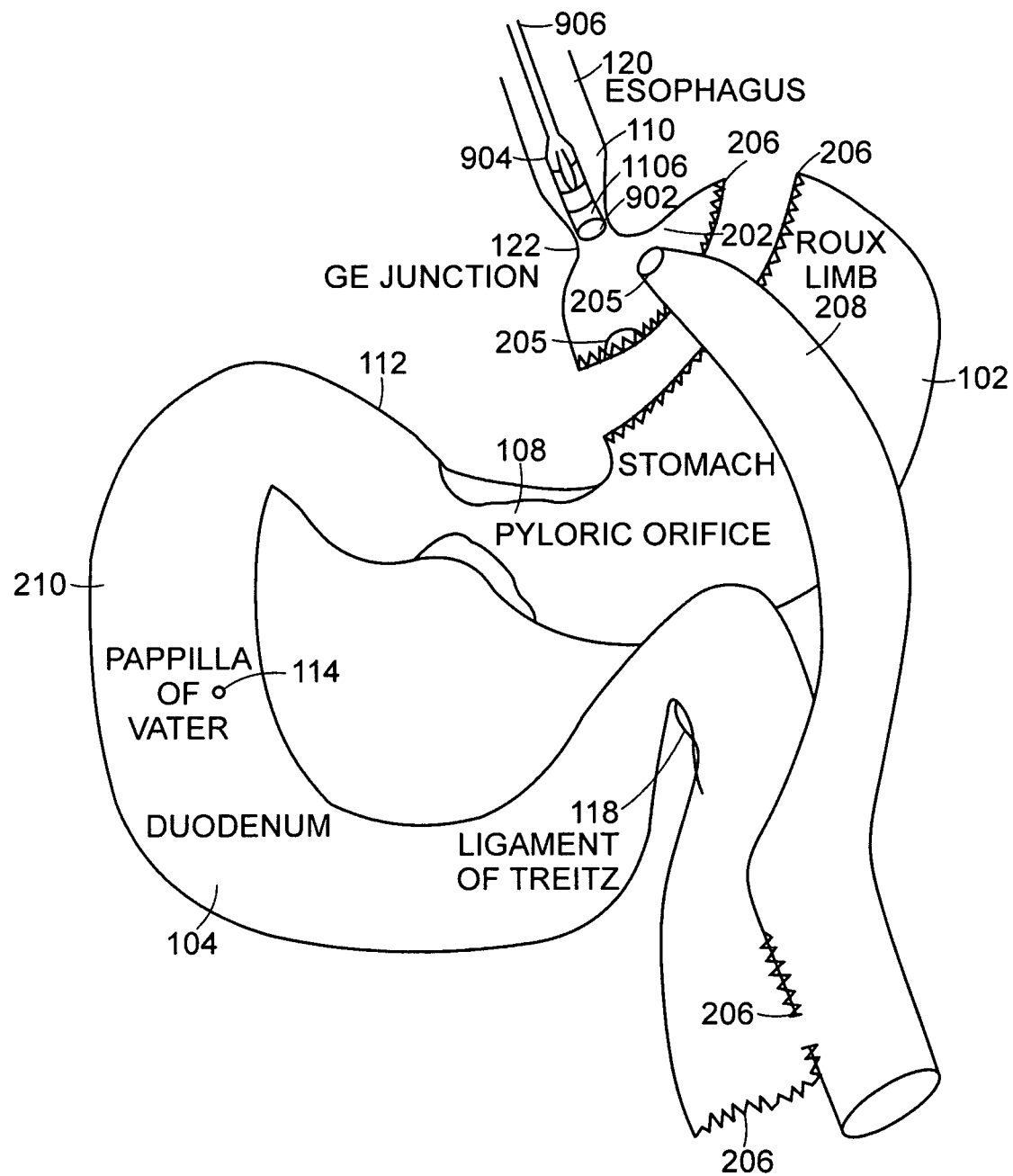

FIGS. 10A-10B are snapshot diagrams illustrating example embodiments of methods of the invention. A gastro-scope (not shown) is directed through the mouth of a patient, and into the esophagus 120. A length of guidewire (not shown) is directed through the working channel of gastro-scope (not shown), out of the distal end, and into the proximal portion of the esophagus. Once a sufficient length of guidewire is in the desire location, gastro-scope can be removed while guidewire is held in position.

Once the guidewire is in the desired location and the gas-tro-scope has been removed, a delivery catheter is directed into the esophagus. The leading or distal end of outer catheter 906 is attached, assembled to, or comprises a capsule or container assembly that includes capsule or container 904. Container 904 defined a guidewire lumen along its side. The proximal end of guidewire is directed through the guidewire lumen, and catheter 906 is advanced or directed along guidewire to a point distal from the GE Junction 122 and into a desired position in the esophagus. Optionally, the location of capsule 904 is confirmed using fluoroscopy.

Once container 904 is at the desired location in the esopha-gus, guidewire can be removed from the esophagus, as illus-trated in FIG. 10A with the guidewire removed. Optionally, prior to insertion, a lubricating jelly is applied to the surface of those portions of catheter 906 that are inserted into the esophagus.

The container holds or houses parts or all of a gastrointes-tinal implant device (e.g., a gastrointestinal sleeve). The gas-trointestinal implant device includes a distal portion and a proximal portion. The distal portion includes a gastrointesti-nal sleeve and the proximal portion of the device includes an anchor for securing the device within the esophagus. In some embodiments, the container holds or houses the proximal portion of the gastrointestinal device. In other embodiments, the container holds or houses both the distal and proximal portions. In still further embodiments, the container holds or houses the entire gastrointestinal device. Some or all of the sleeve portion can be folded and stored in the container with the anchor.

After container 904 is at the desired location in the esopha-gus, a distal portion 1106 of the sleeve is removed from the container and directed into a location in the esophagus that is distal from the container. Outer catheter 906 defines an inner catheter lumen, and an inner catheter, to which ball 902 is releasably attached, is directed through the inner catheter lumen and into locations of the esophagus that are distal from container 904 and esophagus.

For more details regarding the delivery of the gastrointes-tinal implant devices 400, 800, reference U.S. patent appli-cation Ser. No. 11/057,861 filed Feb. 14, 2005, entitled "Methods and devices for placing a gastrointestinal sleeve," U.S. patent application Ser. No. 11/302,977 filed Dec. 13, 2005, entitled "Atraumatic delivery devices," U.S. patent application Ser. No. 11/001,794 filed Nov. 30, 2004, entitled "Bariatric sleeve delivery devices," and U.S. Pat. No. 7,122,058 filed Dec. 2, 2003, entitled "Anti-obesity devices," which are hereby incorporated by reference in their entireties.

FIG. 11 is a schematic diagram showing an exemplary embodiment of a repositioning and retrieval device for the gastrointestinal implant device 400, 800. The repositioning and retrieval device can be used to remove the sleeve and anchor transorally through the mouth once the leaks and/or fistulas have healed. The repositioning and retrieval device 1100 may include a handle 1110 adapted to attach to an actuator 1120 for maneuvering the actuator 1120. The repo-sitioning device 1100 further may include an elongated mem-ber 1150. The actuator 1120 is adapted to attach to a proximal end of the elongated member 1150. The repositioning device 1100 further may include an elongated tube 1140. The elon-gated tube 1140 defines a lumen within which the elongated member 1150 is slidably disposed. The elongated tube 1140 is adapted for insertion into a natural bodily lumen.

A grasper 1160 is coupled at a distal end of the elongated member 1150 and is adapted to grasp a feature of an implant-able device 400, 800. For example, a drawstring 705 can be provided such that manipulation of the drawstring 705 can reduce at least one dimension (e.g., the diameter) of the implantable device 400, 800.

The proximal end of the elongated member 1150 is coupled to the actuator 1120. Similarly, a proximal end of the elongated tube 1140 is coupled to the handle 1110. The handle 1110 and the actuator 1120 may be operated manually from a site external to a body. For example, the handle 1110 and the actuator 1120 can be used to maneuver the elongated member 1150.

The repositioning device 1100 may further include an outer tube 1130. The outer tube 1130 also defined a lumen within which the elongated tube 1140 may be slidably disposed.

In some embodiments, the retrieval hood 1190 is coupled to the outer tube 1140 using an interference fit. In other embodiments, the retrieval hood 1190 may be coupled to the outer tube 1140 using alternative mechanical, chemical, or bonding techniques.

FIG. 12 is a snapshot schematic diagram showing an exem-plary embodiment of the invention capturing a proximal por-tion of an implantable device. The grasper is adapted to grasp a portion of the implantable device, such as a drawstring of a gastrointestinal liner or stent. When the drawstring is grasped and moved linearly, at least a portion of the implantable device radially collapses. The grasped device can then be repositioned within the natural bodily lumen. In some instances, the grasped device can be removed from the natural bodily lumen together with the inner tube. The grasper may be a hook or other structure that is capable of grasping a portion of the implantable device, such as a drawstring. A shown in FIG. 12, the grasper 1160 extending distally beyond the inner tube 1240, engages a portion of the drawstring 705 of the implantable device 400. The actuator 1120 is then used to proximally draw the grasper 1160 and the engaged portion of the drawstring 705 (as indicated by arrow I). For more details regarding the removal and repositioning devices, reference U.S. patent application Ser. No. 11/318,083 filed Dec. 22, 2005, entitled "Removal and repositioning devices," which is hereby incorporated by reference in its entirety.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method of treatment of a fistula or leak of a Roux-en-Y patient comprising the steps of:
    selecting a Roux-en-Y patient having a fistula or leak as a result of bariatric surgery;
    providing an implant comprising a collapsible, self-expanding anchor coupled to a proximal portion of a flexible, floppy sleeve, open at both ends, a distal portion of the flexible, floppy sleeve extending beyond the anchor and being unsupported;
    positioning the anchor within the esophagus of the patient, who has had a Roux-en-Y gastric bypass procedure, and above the gastroesophageal (GE) Junction of the patient; and
    extending the flexible, floppy sleeve through a stomach pouch of the patient past the fistula or leak into an intestine anastomosed to the stomach pouch.

2. The method of claim 1 wherein the anchor is a stent.

3. The method of claim 1, wherein the anchor has a relaxed diameter of 20 to 40 millimeters.

4. The method of claim 1, wherein the anchor has a length of 25 to 40 millimeters.

5. The method of claim 1, wherein the anchor is a wave anchor.

6. The method of claim 1, wherein the anchor is covered with a membrane.

7. The method of claim 1, wherein the anchor is sandwiched between a first inner layer of membrane and a second outer layer of membrane.

8. The method of claim 1, wherein the implant has a length of at least 150 mm.

9. The method of claim 1, wherein the sleeve and anchor are delivered using an esophageal catheter.

10. The method of claim 1, wherein the sleeve and anchor are removed transorally through the mouth.

11. The method of claim 1, wherein the anchor includes a drawstring to facilitate the removal of the anchor.

12. The method of claim 1, wherein the sleeve shields fistulas and leaks from making contact with food and fluids entering the esophagus.

* * * * *